United States Patent
Sigillo et al.

(10) Patent No.: US 8,039,272 B2
(45) Date of Patent: Oct. 18, 2011

(54) RAPID QUANTIFICATION ASSAY INVOLVING CONCENTRATED AND LIGAND-COATED GOLD COLLOID

(75) Inventors: Eric C. Sigillo, Marlborough, MA (US); Jeffrey C. Chien, Wellesley, MA (US); Mary C. Pomeroy, Framingham, MA (US); Catherine A. Saltalamacchia, Winchester, MA (US)

(73) Assignee: Nova Biomedical, Waltham, MA (US)

( * ) Notice: Subject to any disclaimer, the term of this patent is extended or adjusted under 35 U.S.C. 154(b) by 391 days.

(21) Appl. No.: 12/416,570

(22) Filed: Apr. 1, 2009

(65) Prior Publication Data

US 2010/0255610 A1    Oct. 7, 2010

(51) Int. Cl.
*G01N 33/553*    (2006.01)
(52) U.S. Cl. ......... 436/525; 436/164; 436/524; 436/805
(58) Field of Classification Search .................. None
See application file for complete search history.

(56) References Cited

U.S. PATENT DOCUMENTS

| | | | | |
|---|---|---|---|---|
| 4,313,734 A | * | 2/1982 | Leuvering | 436/525 |
| 5,079,172 A | * | 1/1992 | Hari et al. | 436/518 |
| 5,102,788 A | * | 4/1992 | Cole | 435/7.9 |
| 5,514,602 A | * | 5/1996 | Brooks et al. | 436/525 |
| 2003/0157732 A1 | | 8/2003 | Baker et al. | |

FOREIGN PATENT DOCUMENTS

| | | |
|---|---|---|
| EP | 0 587 008 | 2/1999 |
| EP | 0 654 670 | 1/2001 |
| EP | 1 302 770 | 4/2003 |
| JP | 2004-294157 | 10/2004 |
| WO | 98/37417 | 8/1998 |
| WO | 2006/105111 | 10/2006 |

OTHER PUBLICATIONS

Batten, T.F.C. and Hopkins, C.R., "Use of Protein A-coated Colloidal Gold Particles for Immunoelectronmicroscopic Localization of ACTH on Ultrathin Sections", *Histochemistry*, 60:317-320 (1979).

* cited by examiner

*Primary Examiner* — Chris L Chin
(74) *Attorney, Agent, or Firm* — Occhiuti Rohlicek & Tsao LLP

(57) ABSTRACT

A concentrated and ligand-coated gold colloid and a method of preparing it. Also disclosed is a rapid biomolecule quantification assay involving the use of the concentrated gold colloid and an apparatus for performing the assay.

30 Claims, 1 Drawing Sheet

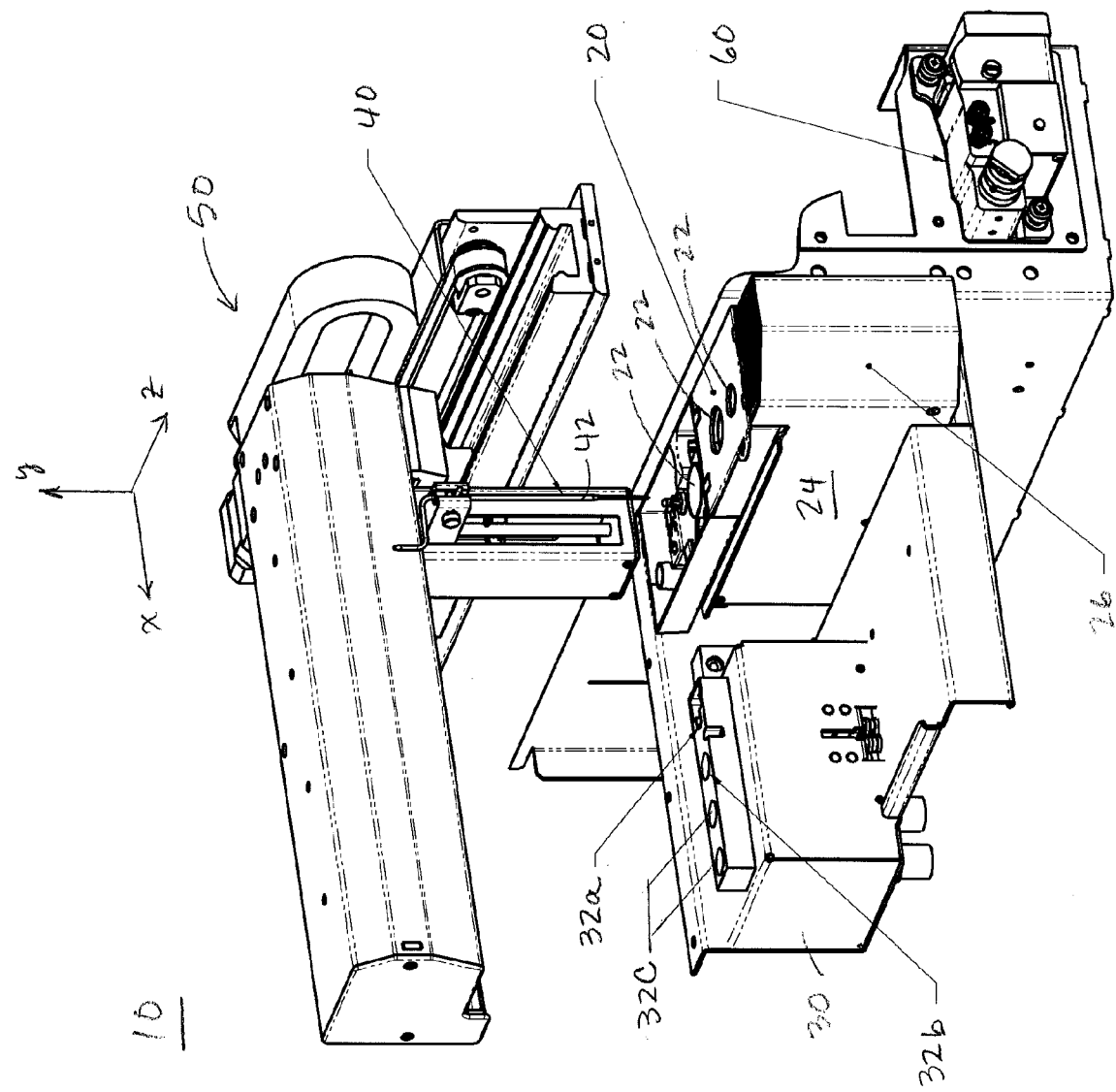

RAPID QUANTIFICATION ASSAY INVOLVING CONCENTRATED AND LIGAND-COATED GOLD COLLOID

BACKGROUND OF THE INVENTION

Many processes have been developed to produce biomolecules, particularly proteins, for various uses. The amount of a biomolecule produced in such a process is an essential parameter for monitoring the progress of that process and assessing its efficiency. Conventional quantification methods, e.g., ELISA and HPLC, normally take several hours to several days. Thus, it is highly desirable to develop a new method for rapid quantification of a target biomolecule.

SUMMARY OF THE INVENTION

In one aspect, the present invention features a composition containing gold particles coated with a protein ligand (e.g., Protein A, Protein G, Protein A/G, Protein L, an antibody, a cell surface receptor, and a lectin). Optionally, it further contains a surfactant. In this composition, the concentration of the gold particles is $0.7 \times 10^{12}$ to $9.0 \times 10^{12}$ particles/ml and that of the protein ligand is 0.002-1.3 nmol/ml (preferably 0.002-0.82 nmol/ml and more preferably 0.002-0.23 nmol/ml). The gold particles typically have an average size of 20-40 nm.

In another aspect, this invention provides a method of preparing the composition described above. This method includes at least three steps: (i) providing a gold colloid containing gold particles at a concentration of $0.7 \times 10^{12}$ to $9.0 \times 10^{12}$ particles/ml, (ii) contacting the gold particles with a protein ligand at a pH equivalent to the isoelectric point of the protein ligand to form a coated gold colloid, and (iii) collecting the coated gold colloid, preferably without removing unbound protein ligand molecules. In the contacting step, the gold particles and the protein ligand molecules are mixed at a ratio of $(0.7-9.0) \times 10^{12}$ particles: 0.002-1.3 nmol ligand. After the contacting step and before the collecting step, the coated gold colloid can be mixed with a stabilizer (e.g., bovine serum albumin) to stabilize the protein ligand coating on the gold particles. If desired, the protein ligand can be mixed with a surfactant before contacting the gold particles. When Protein A is used, the contacting step of this method can be performed at a pH of 5-7 (e.g., 6.2).

Also within the scope of this invention is a method for quantifying a biomolecule using the composition described above, the gold particles in which are coated with a protein ligand specifically binding to the biomolecule. This method includes the steps of (i) providing the composition, (ii) mixing the composition with a sample suspected of containing the biomolecule to form a mixture, (iii) measuring the optical density (OD) of the mixture at a wavelength ranging from 540 to 700 nm (e.g., 590 nm), and (iv) determining the concentration of the biomolecule based on the OD value. The measuring step can be carried out at ambient temperature to 45° C. (e.g., 37-43° C.). In one example, the gold particles in the colloidal composition are coated with Protein A, Protein G, Protein A/G, Protein L, or an anti-immunoglobulin antibody for quantifying an immunoglobulin (Ig), which can be a human, humanized, chimeric, mouse, rat, rabbit, or goat Ig. In another example, the gold particles are coated with a lectin for quantifying a glycoprotein. The gold particles can also be coated with an antibody that specifically binds to a target biomolecule.

The details of one or more embodiments of the invention are set forth in the description below. Other features or advantages of the present invention will be apparent from the following drawing and detailed description of several embodiments, and also from the appended claims.

BRIEF DESCRIPTION OF THE DRAWINGS

FIG. 1 is a perspective view of an apparatus for performing the rapid quantification assay of this invention.

DETAILED DESCRIPTION OF THE INVENTION

The present invention relates to a rapid quantification assay that involves a colloidal gold composition for monitoring the amount of a biomolecule produced in a preparation process, such as a bioprocess (e.g., cell culture or fermentation) or a chemical synthetic process. Biomolecules are organic molecules produced by living organisms, including large polymeric molecules (e.g., proteins, polysaccharides, and nucleic acids) and small natural products (e.g., lipids, metabolites, vitamins, and sterols). The term "gold colloid" or "colloidal gold composition" used herein refers to a suspension of sub-micrometer-sized gold particles evenly dispersed in a fluid (e.g., water or an aqueous buffer).

The colloidal gold composition utilized in the quantification assay of this invention contains highly concentrated gold particles, which are coated with a protein ligand. The ratio between the gold particles and the protein ligand is $(0.7-9.0) \times 10^{12}$ gold particles: 0.002-1.3 nmol protein ligand. In one example, the colloidal gold composition has a gold particle concentration ranging from $3.5 \times 10^{12}$ to $7.0 \times 10^{12}$ particles/ml, e.g., $(3.5-5.25) \times 10^{12}$ particles/ml. When the gold particle concentration in the colloid is $3.5 \times 10^{12}$ particles/ml, the ligand concentration can range from 0.01-0.5 nmol/ml (e.g., 0.01-0.32 nmol/ml, or 0.01-0.088 nmol/ml). These ligand concentration ranges can be adjusted proportionally based on the increase or decrease of the gold particle concentration.

A protein ligand can be a polypeptide or an oligopeptide that specifically binds to a biomolecule (e.g., a protein, a nucleic acid, a polysaccharide, or a lipid). It also can be a conjugate containing a peptide moiety and a carrier (e.g., biotin, hapten, or a drug). The type of the protein ligand contained in the gold colloid depends on the type of the biomolecule to be quantified. For example, when an antibody is the target biomolecule, the protein ligand can be Protein A, Protein G, Protein A/G, Protein L, the antigen to which the antibody specifically binds, or another antibody that specifically binds to Ig. An antibody is an Ig molecule derived from a suitable source (e.g., human, rat, mouse, rabbit, goat, horse, sheep, monkey or another primate, dog, guinea pig, and donkey). It can be a naturally occurring Ig (e.g., IgG, IgA, IgE, IgD, and IgM) or a generically modified Ig (e.g., a humanized or chimeric Ig). In another example, a lectin (e.g., concanavalin A, phytohaemagglutinin, and wheat germ agglutinin) is used for quantifying a glycoprotein as lectins specifically bind to the sugar moieties in a glycoprotein. The protein ligand can also be an antibody specific to a biomolecule (e.g., a protein, a nucleic acid, a polysaccharide, or a lipid).

Preferably, the colloidal gold composition further contains a suitable surfactant. Presence of surfactant precludes the requirement of removing trace amounts of salts contained in the composition as surfactant minimizes flocculation of the composition caused by the salts. Examples of suitable surfactants include Triton X-100, SDS, Tergitol, Brij, Zonyl, Igepal, Tween, and NP-40. When Triton X-100 is used, its concentration can range from 0.001% to 1%.

The colloidal gold composition described above can be prepared as follows:

A highly concentrated gold colloid can be produced by mixing a first solution containing a gold precursor salt (e.g., tetrachloroaurate III trihydate) at a concentration $\geq$5% and a second solution containing an acidic salt (e.g., sodium citrate dihydrate) at a final concentration of $\geq$0.14%. The concentrations of the gold precursor salt and the acidic salt, taken together, determine the concentration of the gold particles in the resultant gold colloid. For example, the gold particle concentration reaches $3.5 \times 10^{12}$ particles/ml when the concentration of the gold precursor salt is 5% and the final concentration of the acidic salt is 0.145%. An increased gold particle concentration can be achieved when higher concentrations of both the gold precursor salt and the acidic salt are utilized.

The average size (i.e., diameter) of the gold particles prepared by the method described above can be measured by conventional methods, e.g., electron microscopy and quasi-elastic light scattering. Preferably, the gold particles have an average diameter of 20-40 nm. Particle size can be controlled by adjusting the amount of the acidic salt used in preparing the gold colloid. More specifically, a lower amount of the acidic salt results in larger gold particles. Particle size can also be affected by the concentration of the gold precursor salt. Namely, a higher concentration of the gold precursor salt results in larger sized particles.

Next, the gold colloid described above is mixed with a protein ligand under conditions suitable for coating of the protein ligand onto the gold particles. Preferably, the protein ligand is pre-mixed with a surfactant. The coating process can be carried out for up to fifteen minutes at a pH value equivalent to the isoelectric point (pI) of the protein ligand (i.e., pI$\pm$2). A very low amount of a protein ligand can be used in this coating process. For example, only 0.01 nmol of a protein ligand is needed to coat $3.5 \times 10^{12}$ gold particles. Given this low amount, any negative effect caused by unbound protein ligand can be ignored. Thus, no washing step may be needed after coating to remove unbound molecules of the ligand.

In one example, the gold particles are coated with an antibody against human IgG as follows. The gold colloid is mixed with 0.1 M N-cyclohexyl-2-aminoethanesulfonic acid buffer to reach a pH value of 8.4. An anti-human IgG antibody (10 μg/ml) is added to the mixture dropwise while stirring. After being incubated for 30 minutes at ambient temperature, the mixture is combined with an acidic solution [e.g., 1N HCL, 1M 2-(N-morpholino)ethanesulfonic acid, or 1M glycine] to lower its pH to 7.4. An aqueous solution containing 10% BSA (w/v, pH 7.4) is then added to the mixture to obtain a solution having a final BSA concentration of 0.1%. Optionally, this solution is washed twice via centrifugation with 0.01M 4-(2-hydroxyethyl)-1-piperazineethanesulfonic acid buffer (pH 8.0) containing 0.1% Triton X-100. After the final round of centrifugation, the pellet is re-suspended to 50% of the original volume in 0.01M HEPES buffer. The anti-human IgG antibody used for coating can be purchased from commercial vendors, such as Sigma, Fitzgerald Industries International, Advanced Immunochemical, Bethyl, Capricorn, Biogenesis, or QED Bioscience. The antibody, either polyclonal or monoclonal, can be derived from mouse, goat, rabbit, or any other suitable source. In one example, the antibody binds to the Fc region, the heavy chain, the light chain of the target human IgG, or the heavy and light chains as a whole. In another example, the antibody targets the intact IgG or its antigen-binding site.

In another example, a lectin (e.g., wheat germ agglutinin or ConA) is used to coat the gold particles. Triton X-100 at a concentration of $\geq$0.01% is preferred to stabilize the coating.

The ligand-coated colloidal gold composition can be mixed with a stabilizer that stabilizes the attachment of the protein ligand on the gold particles. The stabilizer also blocks other reagents (e.g., salts) from binding to the gold particles at places not covered by the protein ligand and prevents the colloidal composition from flocculation. Examples of the stabilizer include BSA, SeaBlock provided by East Coast Biologics, Stable Coat, Stabilizyme, and Stable Coat Concentrate, all provided by Surmodics.

The protein ligand-coated colloidal gold composition can be used to quantify a biomolecule contained in a test sample, which can be derived from a bioprocess for producing the biomolecule. Briefly, a sample containing the target biomolecule is subjected to suitable-fold dilution and the diluted sample is mixed with the protein ligand-coated colloidal gold composition to form a mixture. Upon mixing, the biomolecule binds instantaneously to the protein ligand. The mixture is then examined to determine its OD value at 540-700 nm (e.g., 570-610 nm) at ambient temperature to 45° C. The concentration of the biomolecule is determined by comparing the OD value of the mixture to a calibration curve (see Example 3 below).

The quantification assay described above possesses at least the following advantages. First, it is close to real time in output of a quantification result. More specifically, the whole assay can be completed within three minutes. Second, this assay is very sensitive, e.g., capable of determine an antibody having a concentration ranging from 0.01-5.0 mg/ml. Finally, this assay is compatible with most reagents used in a bioprocess (e.g., cell culture or fermentation) for producing a biomolecule. Thus, samples obtained from a bioreactor or a fermentator can be analyzed by this assay without any pre-treatment, for example, removing cells or cell debris contained therein.

Referring to FIG. 1, quantification assays such as the one described above can be performed using an assay system 10 for quantifying the concentration of a biomolecule in a test sample. The system 10 includes a reagent pack 20, a mixing and dilution platform 30, a system probe 40, a probe positioning device 50, and an optical analysis module 60.

The reagent pack 20 includes one or more vessels 22 for storing reagents. For example, in some embodiments, vessels 22 are provided for storing a cleaning solution, a buffer, a gold colloid as described above, and a calibrator (i.e., a standard of the biomolecule to be quantified). In some approaches, the vessels 22 are arranged in a cartridge 24, and the cartridge 24 is configured to permit temperature control of one or more of the vessels 22. For example, the cartridge 24 includes a reagent refrigeration module 26 to provide refrigeration of the gold colloid.

The mixing and dilution platform 30 includes one or more wells 32 to provide multiple locations at which the reagents can be diluted, temporarily stored, mixed with one or more other reagents, et cetera, as required by the method steps of the particular assay being performed. For example, in some approaches, the platform includes a probe wash and waste well 32a to permit washing of the probe and/or disposal of probe contents, a dilution well 32b to permit dilution of a reagent prior to mixing, and one or more mixing wells 32c to permit mixing of reagents. Each well 32 has an open upper end and a lower end that is connected to a fluid passageway (not shown) that leads to one or both of a waste receptacle (not shown) or the optical analysis module 60. Fluid flow through each fluid passageway is valve controlled (valves not shown) so that fluid may be maintained within the corresponding well 32 or permitted to drain into the corresponding passageway.

In some approaches the platform is configured to permit temperature control of one or more of the wells.

The system probe 40 may include a syringe pump (not shown) connected to a syringe 42 to permit accurate, selective withdrawal, transfer, and release of desired quantities of reagents between the storage vessels 22 and the wells 32 and between the respective wells 32a, 32b, 32c. The syringe pump is a conventional syringe pump, such as those sold by Tecan, Hamilton, and Cavro.

The system probe 40 is mounted to the probe positioning device 50, which is a processor-controlled device (processor not shown) that moves the system probe 40 between the storage vessels 22 and the wells 32, and between respective wells 32a, 32b, 32c. In the illustrated embodiment, the positioning device 50 permits automated motion of the system probe 40 along three orthogonal axes.

The system 10 further includes an optical analysis module 60. In some embodiments, a test sample to be assayed is transferred to the optical analysis module 60 via one of the fluid passageways connected to the wells 32. In other embodiments, the system probe 40 is used to transfer the test sample from the corresponding mixing wells 32c directly to the optical assay module 60. In any case, the test sample is received within a cuvette (not shown) disposed within the optical analysis module 60, and a photometer (not shown) is used to measure the change in light transmission through the sample, permitting a determination of an OD value of the sample. Then, the concentration of the biomolecule within the test sample can be calculated based on the value of the OD of the test sample. The optical analysis module 60 is a conventional optical analysis module, such as that sold by Nova Biomedical. In some embodiments, the optical analysis module is configured for measuring any OD value at a light transmission wavelength in the range of 540 to 700 nm. In other embodiments, the optical analysis module 60 is configured for measuring the OD value at only one light transmission wavelength, e.g., 590 nm.

The system 10 described above is suitable for providing an assay of a single sample of a biomolecule. Simultaneous assays of multiple samples of a biomolecule can also be achieved by modifying system 10 to perform multiple assays in parallel, for example by delivering the samples to be assayed to an array of wells provided in a "plate reader" type optical analyzer.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

Example 1

Preparation of Highly Concentrated Gold Colloid 1.0 gram hydrogen tetrachloroaurate III trihydate was dissolved in 2 liters of water. The solution thus formed was boiled at approximately 103-105° C. and the $Au^{3+}$ contained therein were reduced by addition of 58 ml sodium citrate dihydrate (5% w/v). A gold colloid formed during the reduction process. The gold colloid was cooled to ambient temperature for immediate use or sterilized and stored in a sealed container at 4° C. for future use.

The gold colloid prepared by the procedure described above had a dark burgundy color and exhibited a maximum absorbance at 517-522 nm. Based on this peak wavelength range, it was determined that the gold colloid contained gold particles having an average size of 20 nm. The concentration of the gold particles was $3.5 \times 10^{12}$ particles/ml.

Example 2

Coating Concentrated Gold Colloid with Protein A

The gold colloid produced by the method described in Example 1 was mixed with Protein A and Triton X 100 at a ratio of 1 ml gold colloid: 0.9-4.0 μg (0.9-1.8 μg) Protein A: 0.01% (by volume) Triton X 100. The pH value of the mixture was adjusted to 6.2 to allow binding of Protein A onto the gold particles. Fifteen minutes later, BSA was added to the mixture to a final concentration of 20 μg/ml to stabilize the coating and to block reagents, such as salts, from aggregating or flocculating the gold particles. The mixture had been stirred for 30 minutes and then incubated at ambient temperature to allow equilibration of all of its components. Sodium azide was then added to the mixture at a final concentration of 0.05% (w/v) to prevent bacterial growth.

Example 3

Quantification Assay of Human IgG Using Protein A-Coated and Concentrated

Gold Colloid

The Protein-A coated gold colloid prepared following the method described in Example 2 was diluted with an assay buffer containing 0.1M 2-(N-morpholino)ethanesulfonic acid (pH 5.0). The assay buffer and a human IgG sample diluted with the same buffer were used to produce five standards have IgG concentrations of 0, 0.1, 0.5, 1.0, and 2.0 mg/ml. Each of the standards was mixed with the diluted Protein A-coated gold colloid mentioned above to allow binding of IgG to Protein A. The mixtures were then examined for their OD values at 590 nm. A Protein A-IgG dose response curve (i.e., calibration curve) was generated based on the $OD_{590}$ values of the IgG standards versus their IgG concentrations.

Protein A or Protein A/G coated gold colloids were prepared following the same method described in Example 2 above. After being mixed with each of the human IgG standards, their $OD_{590}$ values were determined and standard Protein A- and Protein A/G-IgG dose response curves were generated accordingly.

Protein A-coated gold colloid as mentioned above was used to quantify human $IgG_1$ produced in a conventional bioprocess. Briefly, samples obtained from the bioprocess at various time points were diluted with the assay buffer mentioned above and mixed with the Protein-A coated gold colloid. The mixtures were immediately examined for their $OD_{590}$ values and the concentrations of the $IgG_1$ were determined according to these values as compared with the standard Protein A-IgG dose response curve.

$IgG_1$ concentrations of the same samples were determined by conventional ELISA and HPLC assays. The results obtained from each of the conventional assays were very similar to those determined by the method using the Protein A-coated colloidal gold composition.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A colloidal composition, comprising a plurality of gold particles coated with a protein ligand, wherein the composition has a gold particle concentration of $(0.7-9.0) \times 10^{12}$ particles/ml and a ligand concentration of 0.002-1.3 nmol/ml.

2. The colloidal composition of claim 1, wherein the gold particle concentration is $(3.5-5.25) \times 10^{12}$ particles/ml.

3. The colloidal composition of claim 1, wherein the ligand concentration is 0.002-0.82 nmol/ml.

4. The colloidal composition of claim 3, wherein the ligand concentration is 0.002-0.23 nmol/ml.

5. The colloidal composition of claim 1, wherein the protein ligand is selected from the group consisting of Protein A, Protein G, Protein A/G, Protein L, an antibody, a cell surface receptor, and a lectin.

6. The colloidal composition of claim 3, wherein the protein ligand is Protein A, Protein G, Protein A/G, Protein L, or an antibody specifically binding to an immunoglobulin.

7. The colloidal composition of claim 1, further comprising a surfactant.

8. The colloidal composition of claim 1, wherein the gold particles have an average diameter of 20-40 nm.

9. The colloidal composition of claim 8, wherein the gold particle concentration is $(3.5-5.25) \times 10^{12}$ particles/ml.

10. The colloidal composition of claim 8, wherein the ligand concentration is 0.002-0.23 nmol/ml.

11. The colloidal composition of claim 8, wherein the protein ligand is selected from the group consisting of Protein A, Protein G, Protein A/G, Protein L, an antibody, a cell surface receptor, and a lectin.

12. The colloidal composition of claim 11, wherein the protein ligand is Protein A, Protein G, Protein A/G, Protein L, or an antibody specifically binding to an immunoglobulin.

13. The colloidal composition of claim 8, further comprising a surfactant.

14. A method of preparing a coated gold colloid, comprising
providing a gold colloid containing gold particles at a concentration of $(0.7-9.0) \times 10^{12}$ particles/ml,
contacting the gold particles with a protein ligand at a pH value equivalent to the isoelectric point of the protein ligand to produce a coated gold colloid, wherein the ratio between the gold particles and the ligand is $(0.7-9.0) \times 10^{12}$ particles: 0.002-1.3 nmol, and
collecting the coated gold colloid.

15. The method of claim 14, wherein the collecting step is performed by harvesting the coated gold colloid without removing unbound molecules of the protein ligand.

16. The method of claim 15, wherein the gold particles have an average diameter of 20-40 nm.

17. The method of claim 16, wherein the protein ligand is premixed with a surfactant.

18. The method of claim 16, further comprising mixing the coated golloid with a stabilizer to stabilize coating of the ligand on the gold particles.

19. The method of claim 16, wherein the protein ligand is selected from the group consisting of Protein A, Protein G, Protein A/G, Protein L, an antibody, a cell surface receptor, and a lectin.

20. The method of claim 16, wherein the protein ligand is Protein A, its concentration is 0.002-0.23 nmol/ml, and the pH value is 6.2.

21. A coated gold colloid prepared by the method of claim 15.

22. A method for quantifying a biomolecule, comprising:
providing a colloidal gold composition of claim 1,
mixing the colloidal gold composition with a sample suspected of containing the biomolecule to form a mixture,
measuring the optical density of the mixture at a wavelength ranging from 540-700 nm, and
determining the concentration of the biomolecule based on the value of the optical density.

23. The method of claim 22, wherein the optical density is measured at 590 nm.

24. The method of claim 22, wherein the gold particles have an average diameter of 20-40 nm.

25. The method of claim 24, wherein the colloidal gold composition further contains a surfactant.

26. The method of claim 24, wherein the biomolecule is an immunoglobulin and the protein ligand is Protein A, Protein G, Protein A/G, Protein L, or an antibody specifically binding to the immunoglobulin.

27. The method of claim 26, wherein the immunoglobulin is a human, humanized, chimeric, mouse, rat, rabbit, sheep, monkey, donkey, or goat immunoglobulin.

28. The method of claim 27, wherein the immunoglobulin is immunoglobulin G.

29. The method of claim 22, wherein the biomolecule is a glycoprotein and the protein ligand is a lectin.

30. The method of claim 22, wherein the protein ligand is an antibody that specifically binds to the biomolecule.

* * * * *